(12) United States Patent
Yang et al.

(10) Patent No.: US 10,669,249 B2
(45) Date of Patent: Jun. 2, 2020

(54) ROTIGOTINE BEHENATE, AND MANUFACTURING METHOD AND APPLICATION THEREOF

(71) Applicant: Shandong Luye Pharmaceutical Co., Ltd., Yantai, Shandong (CN)

(72) Inventors: Mina Yang, Shandong (CN); Yongtao Jiang, Shandong (CN); Ying Meng, Shandong (CN); Tao Wang, Shandong (CN); Qian qian Xu, Shandong (CN); Xin Shao, Shandong (CN); Chunjie Sha, Shandong (CN)

(73) Assignee: Shandong Luye Pharmaceutical Co., Ltd., Yantai, Shandong (CN)

( * ) Notice: Subject to any disclaimer, the term of this patent is extended or adjusted under 35 U.S.C. 154(b) by 0 days.

(21) Appl. No.: 16/309,807

(22) PCT Filed: Jul. 21, 2016

(86) PCT No.: PCT/CN2016/090803
§ 371 (c)(1),
(2) Date: Dec. 13, 2018

(87) PCT Pub. No.: WO2018/014277
PCT Pub. Date: Jan. 25, 2018

(65) Prior Publication Data
US 2019/0330177 A1    Oct. 31, 2019

(51) Int. Cl.
*C07D 333/10* (2006.01)

(52) U.S. Cl.
CPC ........ *C07D 333/10* (2013.01); *C07B 2200/13* (2013.01)

(58) Field of Classification Search
CPC .................................................... C07D 333/10

USPC ........................................................... 549/74
See application file for complete search history.

(56) References Cited

FOREIGN PATENT DOCUMENTS

| WO | 2012/068783 A1 | 5/2012 |
| WO | 2013/168033 A1 | 11/2013 |
| WO | 2016/014242 A1 | 1/2016 |

OTHER PUBLICATIONS

International Search Report dated May 2, 2017 for International Application No. PCT/CN2016/090803, 2 pages.

*Primary Examiner* — Nizal S Chandrakumar
(74) *Attorney, Agent, or Firm* — Seed IP Law Group LLP

(57) ABSTRACT

The present disclosure relates to rotigotine behenate, methods for preparing the same and use of the same for treating diseases associated with dopamine receptor. The rotigotine behenate, the structure of which is shown below, is capable of reducing fluctuation in blood drug concentrations, improving the bioavailability of the drug in vivo, and achieving smooth and extended release of rotigotine.

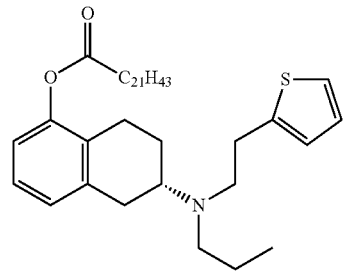

16 Claims, 6 Drawing Sheets

ROTIGOTINE BEHENATE, AND MANUFACTURING METHOD AND APPLICATION THEREOF

TECHNICAL FIELD

The present invention relates to a rotigotine derivative, a preparation method and use thereof, in particular to a rotigotine long-chain ester, a preparation method thereof and use thereof.

TECHNICAL BACKGROUND

Rotigotine is a non-ergot selective dopamine receptor agonist that produces an anti-Parkinson effect by activating D3/D2/D1 dopamine receptors. Due to the first-pass effect of the liver, the oral bioavailability of rotigotine is extremely low (about 1%-5%), which renders it unsuitable for oral administration. Currently there is no cure for Parkinson's disease. Patients thus require long-term treatment or management by drugs. Therefore, it is of great clinical significance to develop a drug characterized by a concise preparation process, low cost, and long-term steady release to improve the drug accessibility.

WO 2012/068783 discloses a rotigotine microsphere preparation capable of maintaining an effective blood drug concentration for more than two weeks. Although the microsphere preparation could achieve the objective of sustained steady release, the preparation process are complicated and accompanied by high production costs.

WO 2016/014242 discloses a series of structurally-modified derivatives of rotigotine, including rotigotine and its esters with saturated long chain of up to 16 carbons, which overcome the defect of low blood drug concentration of rotigotine for oral administration. Nevertheless, such oral dosage forms cannot achieve the objective of sustained steady release for longer than two weeks. Experiments conducted by the inventors of the present invention have revealed that injecting the saturated long-chain esters of rotigotine disclosed in WO 2016014242, such as rotigotine caprylate and rotigotine palmitate, can cause the blood drug concentration to fluctuate significantly. As such, the effective blood drug concentration is maintained for only a short period of time, and the long-term steady release of the drug cannot be achieved.

The inventors of the present invention conducted intensive studies on other saturated and unsaturated long-chain esters of rotigotine, and surprisingly found that only saturated long-chain ester of rotigotine with twenty-two carbons has both long-lasting effective blood drug concentration, high bioavailability, and long-term steady release, whereas saturated or unsaturated long-chain esters of rotigotine with more or fewer than twenty-two carbons do not have the aforementioned excellent effects.

SUMMARY OF THE INVENTION

The present invention provides rotigotine behenate and a preparation method and a use thereof.

The rotigotine behenate provided by the present invention has the following structural formula:

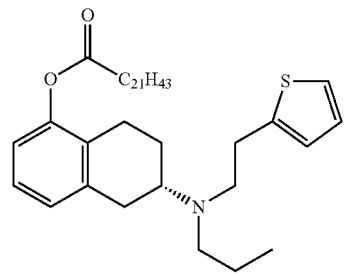

The present invention provides a method for preparing rotigotine behenate, the method comprising: reacting behenoyl chloride with rotigotine to provide rotigotine behenate; or alternatively: reacting behenic acid with rotigotine to provide rotigotine behenate; or alternatively: reacting behenic anhydride with rotigotine to provide rotigotine behenate.

The present invention provides a method for preparing rotigotine behenate: adding rotigotine to a mixture of triethylamine and dichloromethane (DCM) under nitrogen at room temperature, and then adding behenoyl chloride, washing after completion of the reaction, evaporating the solvents under reduced pressure, and purifying to provide rotigotine behenate; or alternatively: dissolving behenic acid, rotigotine and 4-(dimethylamino)pyridinium p-toluene sulfonate (DPTS) in dichloromethane (DCM) under nitrogen at room temperature, adding N,N'-dicyclohexylcarbodiimide (DCC) dropwise to the above mixture, filtering the mixture after completion of the reaction, and evaporating the solvent under reduced pressure and purifying to provide rotigotine behenate; or alternatively: dissolving behenic anhydride and rotigotine in anhydrous tetrahydrofuran (THF) under nitrogen, adding a catalytic amount of triethylamine, heating the mixture in oil bath, and evaporating the solvent under reduced pressure after completion of the reaction, and subsequently adding dichloromethane (DCM), followed by washing with sodium hydrogencarbonate solution, evaporating the solvent under reduced pressure and purifying to provide rotigotine behenate.

The present invention provides a rotigotine behenate crystal form (Form I), which has characteristic peaks at 2θ (2θ (degrees))=21.563, 21.156, 23.295, 21.955 and 20.838 (±0.2 degrees 2θ) in the powder X-ray diffraction pattern obtained by CuKα radiation.

In another embodiment, the rotigotine behenate crystal form (Form I) has characteristic peaks at 2θ (2θ (degrees))=21.563, 21.156, 23.295, 21.955, 20.838, 16.154, 19.403, 11.749, 14.518 and 17.875 (±0.2 degrees 2θ) in the powder X-ray diffraction pattern obtained by CuKα radiation.

In another embodiment, the rotigotine behenate crystal form (Form I) has characteristic peaks at 2θ (2θ (degrees))=21.563, 21.156, 23.295, 21.955, 20.838, 16.154, 19.403, 11.749, 14.518, 17.875, 19.729, 20.299, 13.583, 11.962, 22.949, 23.772, 16.424, 15.749, 12.586 and 22.430 (±0.2 degrees 2θ) in the powder X-ray diffraction pattern obtained by CuKα radiation.

In another embodiment, the rotigotine behenate crystal form (Form I) has characteristic peaks at 2θ (2θ (degrees))=21.563, 21.156, 23.295, 21.955, 20.838, 16.154, 19.403, 11.749, 14.518, 17.875, 19.729, 20.299, 13.583, 11.962, 22.949, 23.772, 16.424, 15.749, 12.586, 22.430, 12.238, 23.995, 18.626, 16.614, 28.574, 24.530, 25.169, 27.044, 36.329, 27.764, 29.127 and 31.490 (±0.2 degrees 2θ) in the powder X-ray diffraction pattern obtained by CuKα radiation.

The rotigotine behenate crystal form (Form I) has a powder X-ray diffraction pattern substantially as shown in FIG. 4.

The rotigotine behenate crystal form (Form I) has TGA/DSC curves substantially as shown in FIG. 6.

The present invention also provides a preparation method for the rotigotine behenate crystal form (Form I): dissolving rotigotine behenate in an organic solvent, cooling and crystallizing, filtering, washing to provide the rotigotine behenate crystal form (Form I), wherein the organic solvent is selected from one or more of ethyl acetate, ethanol, methanol, cyclohexane, n-hexane, petroleum ether, tetrahydrofuran, acetone, n-heptane. Preferably, after the thermal dissolution of rotigotine behenate in ethyl acetate, adding methanol, cooling and crystallizing, followed by filtering and washing with an appropriate amount of methanol.

The present invention further provides a rotigotine behenate crystal form (Form II), which has characteristic peaks at 2θ (2θ (degrees))=21.481, 23.887 (±0.2 degrees 2θ) in the powder X-ray diffraction pattern obtained by CuKα radiation.

Another embodiment provides rotigotine behenate crystal form (Form II) having characteristic peaks at 2θ (2θ (degrees))=3.274, 21.481, 23.887 (±0.2 degrees 2θ) in the powder X-ray diffraction pattern obtained by CuKα radiation One embodiment provides rotigotine behenate crystal form (Form II) having a powder X-ray diffraction pattern substantially as shown in FIG. 5.

One embodiment provides rotigotine behenate crystal form (Form II) having TGA/DSC curves substantially as shown in FIG. 7.

The present invention also provides a preparation method for rotigotine behenate crystal form (Form II), the method comprising: placing rotigotine behenate in a mixed solvent of tetrahydrofuran and methanol to provide a suspension, and stirring the suspension at 40° C. to provide the rotigotine behenate crystal form (Form II).

The present invention provides a pharmaceutical composition comprising rotigotine behenate. In particular, the pharmaceutical compositions provided herein are administered in a parenteral form, preferably by injection, more preferably by intramuscular or subcutaneous injection.

The rotigotine behenate pharmaceutical composition provided by the present invention can achieve a dosing interval of at least about two weeks.

Another aspect provides the rotigotine behenate for use in treating a disease associated with dopamine receptors. In particular, the rotigotine behenate as defined above is used for the treatment of Parkinson's disease.

The rotigotine behenate provided by the present invention may be administered at a daily dose of from 1 mg to 1000 mg in the treatment of the aforementioned related diseases.

The rotigotine behenate provided by the present invention is capable of reducing fluctuation in blood drug concentrations, improving the bioavailability of the drug in vivo, and achieving smooth release of rotigotine for more than two weeks.

DETAILED DESCRIPTION OF EMBODIMENTS

The following examples are intended to illustrate the present invention in more detail, but are not intended to limit the present invention in any way.

Example 1: Rotigotine Behenate

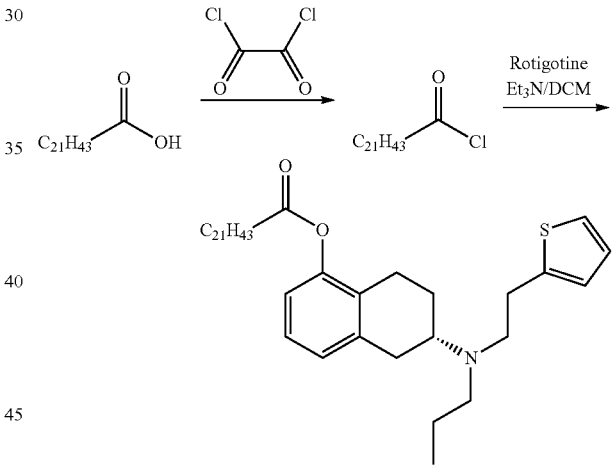

Figure 1:
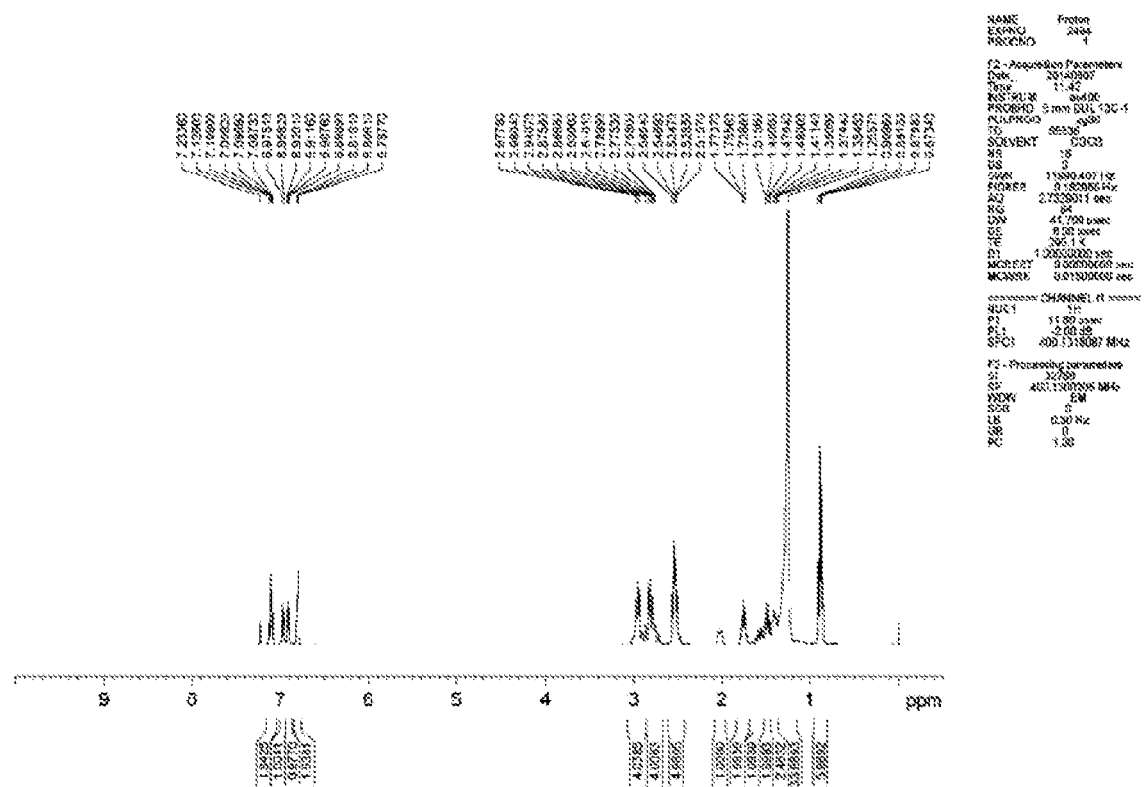
FIG. 1 shows the $^1$H NMR spectrum of rotigotine behenate in Example 1.
Figure 2:
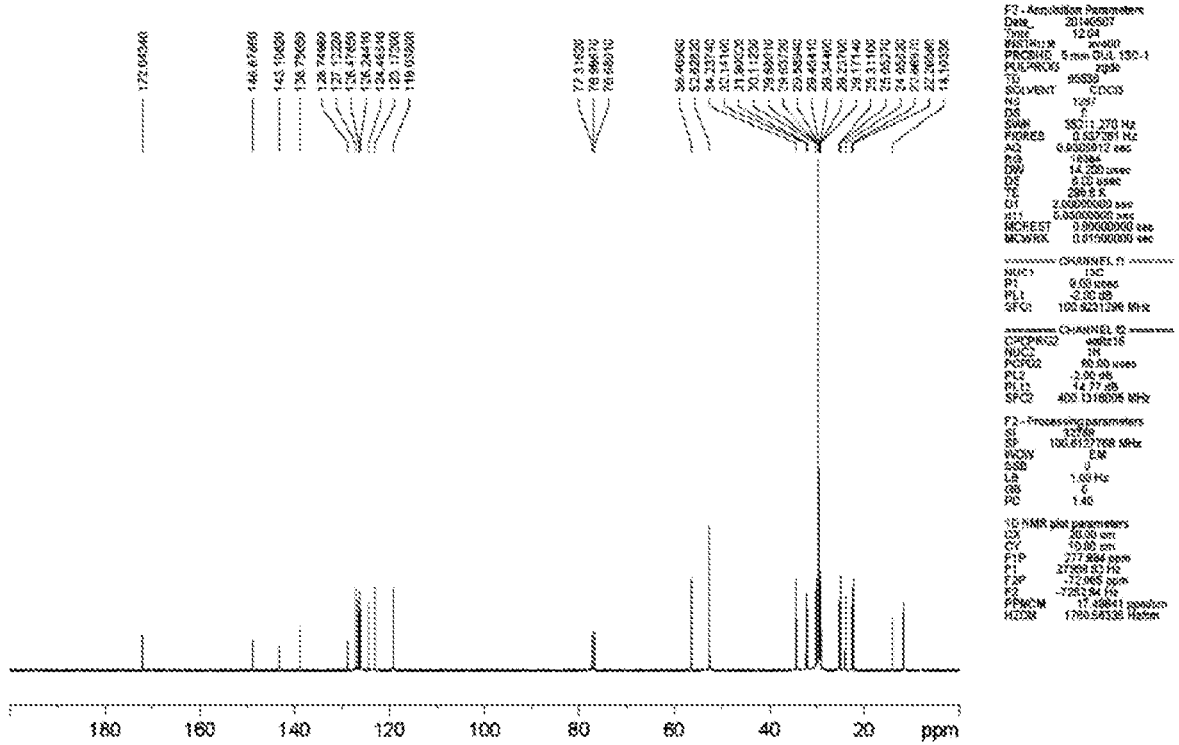
FIG. 2 shows the $^{13}$C NMR spectrum of rotigotine behenate in Example 1.
Figure 3:
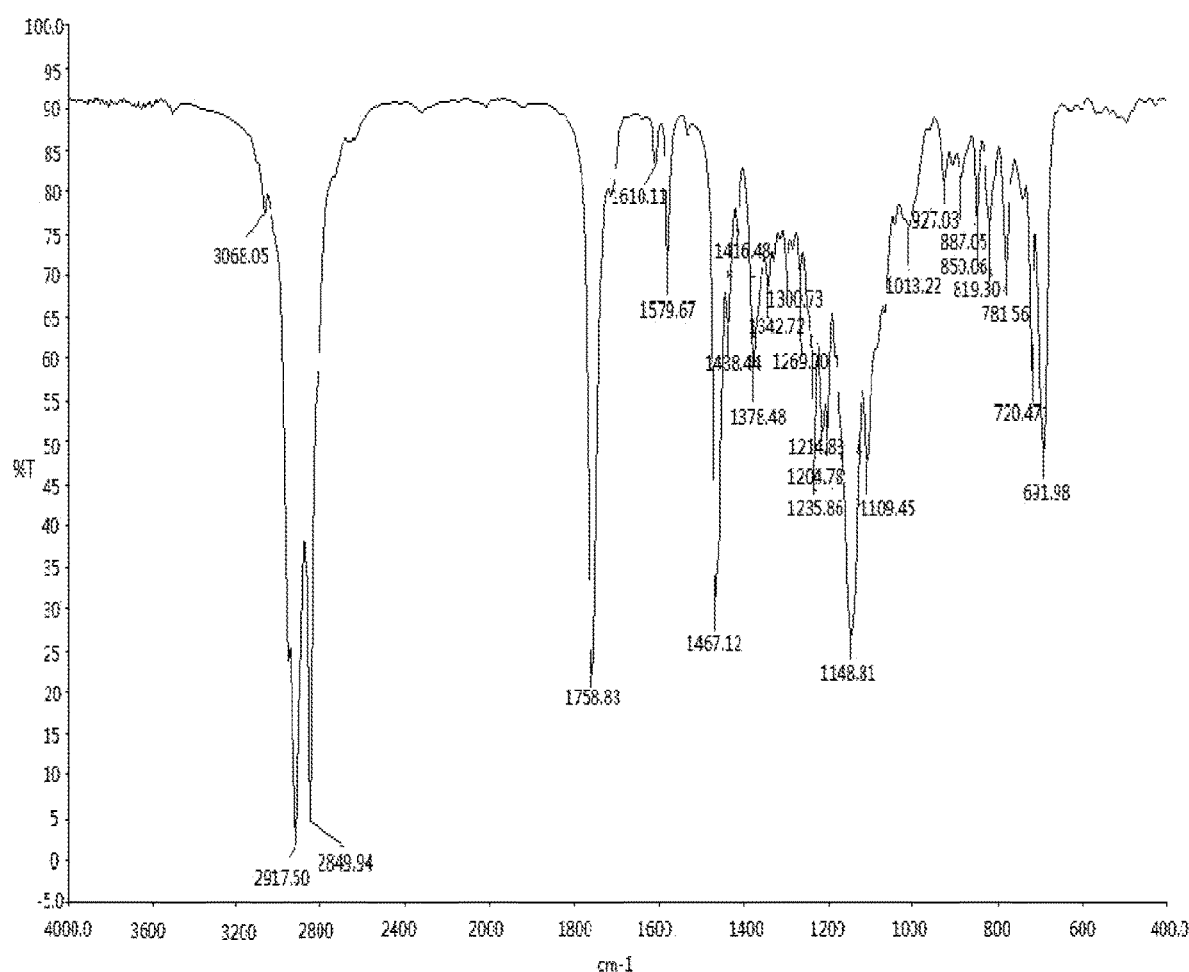
FIG. 3 shows the IR spectrum of rotigotine behenate in Example 1.

34.1 g (0.1 mol) of behenic acid was dissolved in 300 ml of dichloromethane (DCM) under nitrogen at room temperature, and 12.7 g (0.1 mol) of oxalyl chloride was added dropwise to the mixed solution; the resulting solution after completion of the reaction was referred to as Solution I. 31.5 g (0.1 mol) of rotigotine was dissolved in a mixed solution containing 15.2 g (0.15 mol) of triethylamine and 300 ml of dichloromethane (DCM), which was referred to as Solution II. Solution I was added dropwise to Solution II to provide a reaction solution, upon completion of the reaction, the reaction solution was washed with an equal volume of water, and the solvent of the organic phase was evaporated under reduced pressure. The residue was purified by column chromatography, with a 1:3 (v/v) ethyl acetate-petroleum ether system as the eluent, to give a white solid (44.2 g) in a yield of 69.0%, melting point 48-52° C. FIGS. 1 and 2 are the $^1$H NMR and the $^{13}$C NMR spectra of the titled compound, respectively, and FIG. 3 is the IR spectrum of the titled compound.

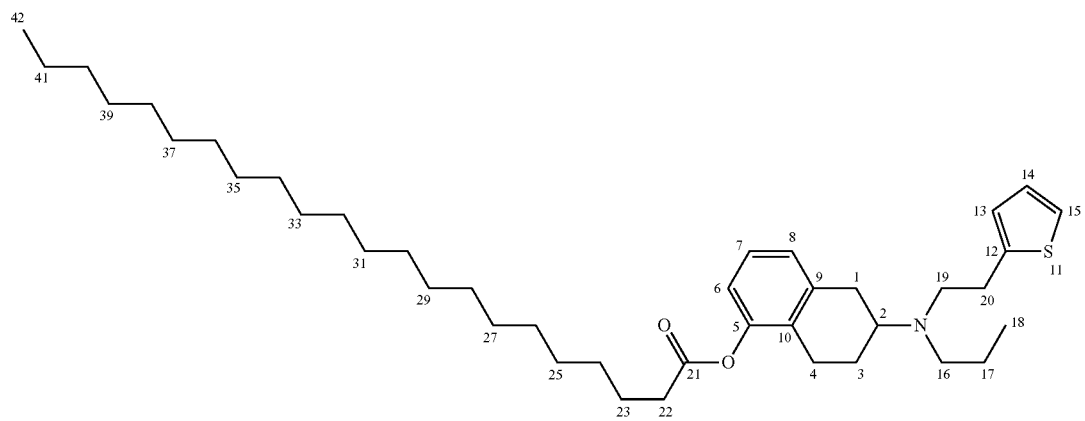 [SMILES: CCCCCCCCCCCCCCCCCCCCCC(=O)Oc1cccc2c1CCC(N(CCC)CCc1cccs1)C2]

$^1$H NMR (CDCl$_3$, 400 MHz) δ$_H$: 7.12 (m, 2H, H-7 & H-14), 6.98 (d, J=7.40 Hz, 1H, H-6), 6.92 (q, J=3.44, 5.04 Hz, 1H, H-15), 6.82 (d, J=7.28 Hz, 2H, H-8 & H-13), □3.01 (m 4H, H-1 & H-4), 2.81 (m, 4H, H-19 & H-20), 2.54 (m, 5H, H-2, H-16 & H-22), 2.08 (m, 1H, H-3), 1.76 (m, 2H, H-23), 1.58 (m, 1H, H-3), 1.39 (m, 2H, H-41), 1.26 (m, 36H, H-17, H-24~H-40), 0.88 (m, 6H, H-18 & H-42);

$^{13}$C NMR (CDCl$_3$, 100 MHz) δ$_C$: 172.0 (C-21), 148.9 (C-5), 143.1 (C-12), 138.8 (C-9), 128.7 (C-10), 127.1 (C-15), 126.5 (C-7), 126.2 (C-13), 124.5 (C-14), 123.1 (C-8), 119.0 (C-6), 56.4 (C-2), 52.6 (2C, C-19 & C-16), 34.2 (C-22), 32.1 (C-40), 31.9 (C-20), 30.1 (C-1), 29.2-29.7 (C-24~C-39), 25.3 (C-3), 25.1 (C-23), 24.1 (C-4), 22.7 (C-41), 22.3 (C-17), 14.1 (C-42), 11.9 (C-18).

Example 2: Rotigotine Behenate

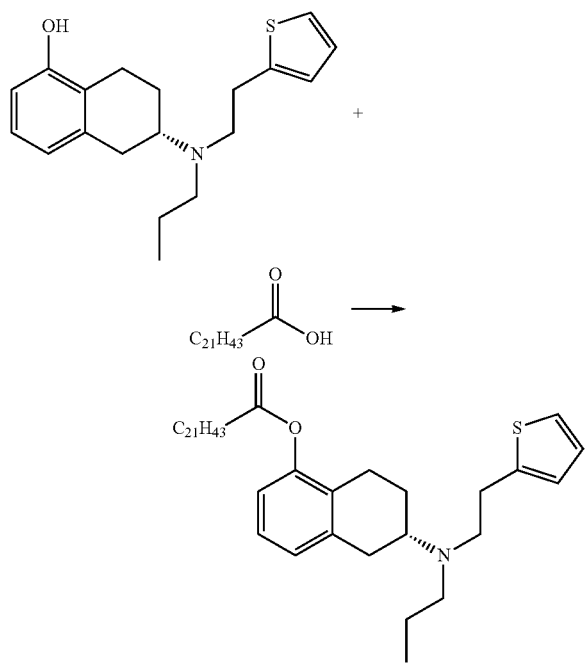

3.4 g (0.01 mol) of behenic acid, 3.1 g (0.01 mol) of rotigotine and 1.4 g (0.005 mol) of 4-(dimethylamino) pyridinium-p-toluene sulfonate (DPTS) were dissolved in 20 ml of dichloromethane (DCM) under nitrogen at 0° C., and 2.7 g (13 mmol) of N,N'-dicyclohexylcarbodiimide (DCC) was added dropwise to the above reaction mixture. The reaction mixture was filtered after completion of the reaction, and the filter cake was washed with an appropriate amount of dichloromethane (DCM). The filtrate was combined, and dichloromethane (DCM) was evaporated under reduced pressure. The residue was purified by column chromatography, with a 1:3 (v/v) ethyl acetate-petroleum ether system as the eluent, to provide a white solid (4.3 g) in a yield of 67%, melting point 48-52° C. The $^1$H NMR, $^{13}$C NMR and IR spectra of the titled compound are identical to those obtained in Example 1.

Example 3: Rotigotine Behenate Crystal Form (Form I)

Rotigotine behenate prepared in Example 1 was dissolved in ethyl acetate by thermal dissolution, and subsequently methanol was added thereto, followed by cooling and crystallization. After filtering, the filter cake was washed with an appropriate amount of methanol to provide a white solid, the structure of which was determined by the following methods:

Test instrument: PANalytical Empyrean X-ray powder diffraction analyzer.

Test conditions: CuKα radiation, Kα1 (Å): 1.540598, Kα2 (A): 1.544426 Kα2/Kα1; Intensity ratio: 0.50, X-ray tube setting: 45 kV 40 mA, divergence slit: automatic, scanning mode: continuous, scanning range (° 2 TH) 3°-40° scanning step (° 2 TH) 0.013 scanning rate (°/min) about 10.

Differential Scanning Calorimetry (DSC)

Instrument: TA Q200/Q2000 Differential Scanning calorimeter provided by TA Instruments:

Method: The sample was placed in an aluminum plate and covered, and was heated from room temperature to a set temperature at a rate of 10° C./min under nitrogen.

Thermogravimetric Analysis (TGA)

Instrument: TA Q500/Q5000 Thermogravimetric Analyzer provided by TA Instruments. Method: The sample was placed in an alloy plate and was heated from room temperature to a set temperature at a rate of 10° C./min under nitrogen.

Figure 4:
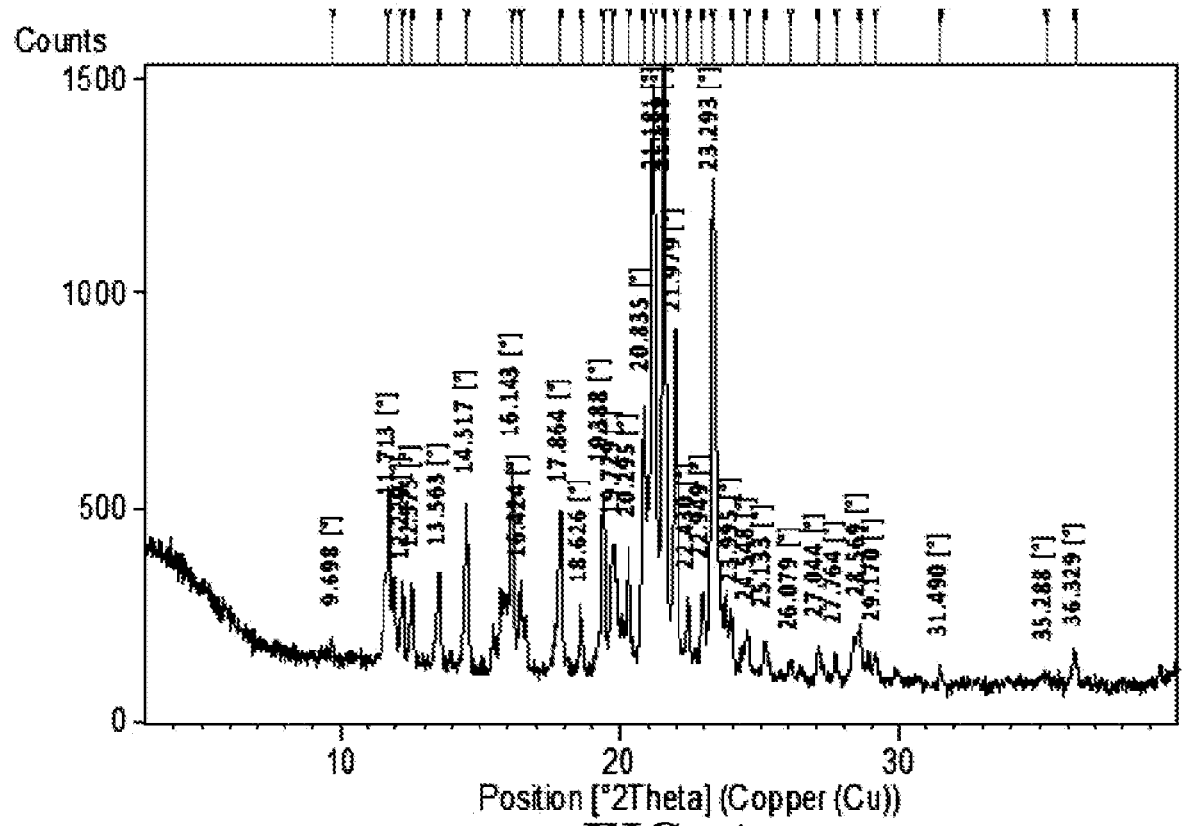
FIG. 4 shows the powder X-ray diffraction pattern of rotigotine behenate crystal form (Form I) in Example 3.
Figure 6:
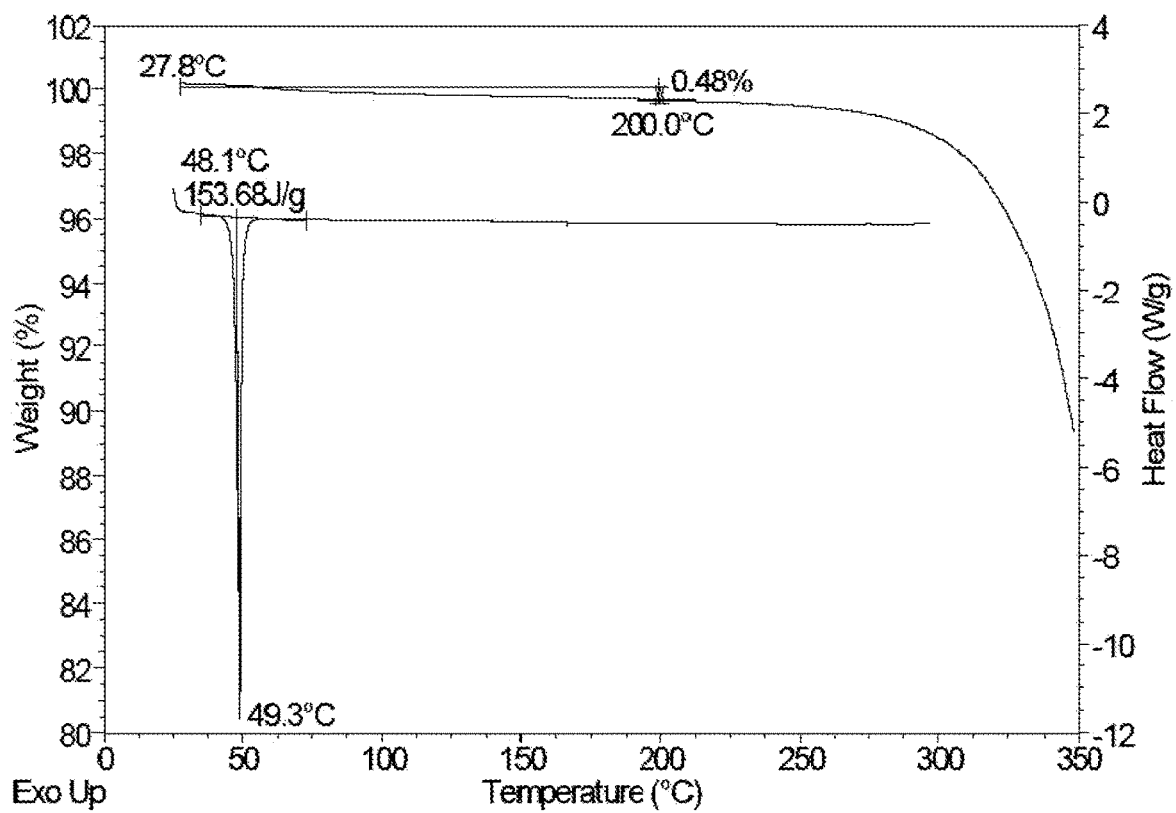
FIG. 6 shows the TGA/DSC curves of rotigotine behenate crystal form (Form I) in Example 3.

Result: the XRPD data of the rotigotine behenate crystal form (Form I) are shown in Table 1, the powder X-ray diffraction pattern is shown in FIG. 4, and the TGA/DSC is shown in FIG. 6.

TABLE 1

Rotigotine behenate crystal form (Form I) XRPD data

| Pos. [°2Th.] | Height [cts] | FWHMLeft [°2Th.] | d-spacing [Å] | Rel. Int. [%] |
|---|---|---|---|---|
| 11.748580 | 412.859000 | 0.089544 | 7.53264 | 28.80 |
| 11.961550 | 204.388100 | 0.076752 | 7.39900 | 14.26 |
| 12.237820 | 156.078000 | 0.089544 | 7.23258 | 10.89 |
| 12.585540 | 174.660100 | 0.089544 | 7.03353 | 12.19 |
| 13.583960 | 218.506400 | 0.102336 | 6.51872 | 15.24 |
| 14.517520 | 388.543600 | 0.127920 | 6.10157 | 27.11 |
| 15.749400 | 179.957200 | 0.076752 | 5.62698 | 12.56 |
| 16.153840 | 461.856900 | 0.089544 | 5.48700 | 32.22 |
| 16.423700 | 182.669800 | 0.102336 | 5.39745 | 12.74 |
| 16.613510 | 124.542100 | 0.076752 | 5.33621 | 8.69 |
| 17.874630 | 385.559900 | 0.089544 | 4.96246 | 26.90 |
| 18.625840 | 130.024200 | 0.102336 | 4.76398 | 9.07 |
| 19.403000 | 420.054300 | 0.115128 | 4.57488 | 29.31 |
| 19.728520 | 290.907200 | 0.179088 | 4.50012 | 20.30 |
| 20.298570 | 288.026100 | 0.115128 | 4.37502 | 20.10 |
| 20.838250 | 626.098000 | 0.089544 | 4.26291 | 43.68 |
| 21.155780 | 1325.514000 | 0.102336 | 4.19964 | 92.48 |
| 21.562650 | 1433.305000 | 0.127920 | 4.12131 | 100.00 |
| 21.955060 | 799.897300 | 0.063960 | 4.04853 | 55.81 |
| 22.430140 | 173.571400 | 0.102336 | 3.96384 | 12.11 |
| 22.948710 | 198.456400 | 0.102336 | 3.87543 | 13.85 |
| 23.294780 | 1152.738000 | 0.127920 | 3.81864 | 80.43 |
| 23.774200 | 195.329500 | 0.076752 | 3.74271 | 13.63 |
| 23.994870 | 145.715100 | 0.102336 | 3.70878 | 10.17 |
| 24.529790 | 98.424370 | 0.255840 | 3.62910 | 6.87 |
| 25.169150 | 85.454170 | 0.153504 | 3.53835 | 5.96 |
| 27.043790 | 70.776630 | 0.153504 | 3.29718 | 4.94 |
| 27.764090 | 55.805020 | 0.153504 | 3.21326 | 3.89 |
| 28.573820 | 122.242000 | 0.358176 | 3.12401 | 8.53 |
| 29.127000 | 54.343720 | 0.307008 | 3.06593 | 3.79 |
| 31.489760 | 31.995680 | 0.153504 | 2.84107 | 2.23 |
| 36.328700 | 58.247280 | 0.204672 | 2.47298 | 4.06 |

Example 4 Rotigotine Behenate Crystal Form (Form II)

The rotigotine behenate prepared in excess in Example 1 was suspended in a mixture of solvents of tetrahydrofuran and methanol at 1:19 (v/v), and the suspension was stirred at 40° C. for 5 days to provide rotigotine behenate crystal form (Form II).

The measurement was carried out in accordance with the methods described in Example 3.

The TGA results showed that the weight loss was 3.1% when the sample was heated to 100° C., and three endothermic peaks were observed in the DSC curve, which were at 30.9° C., 41.7° C., and 46.7° C. (peak values), respectively.

Figure 5:
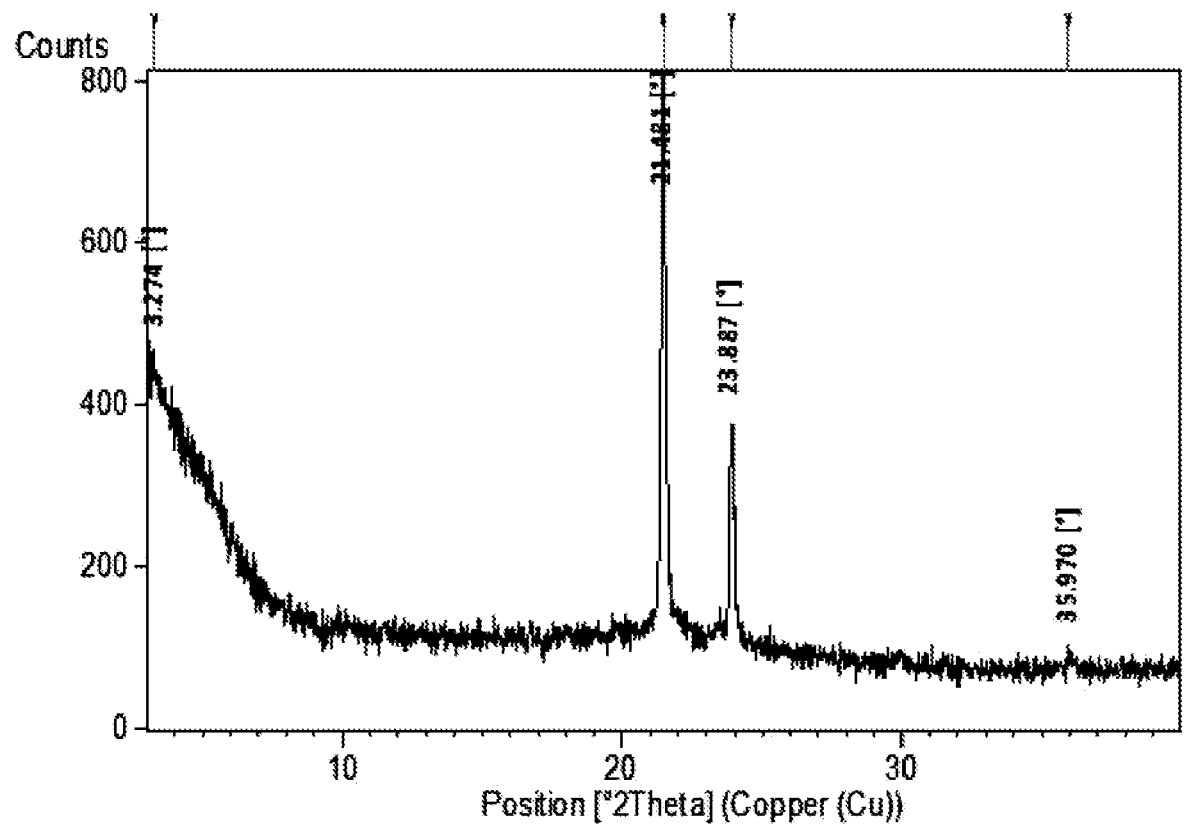
FIG. 5 shows the powder X-ray diffraction pattern of rotigotine behenate crystal form (Form II) in Example 4.
Figure 7:
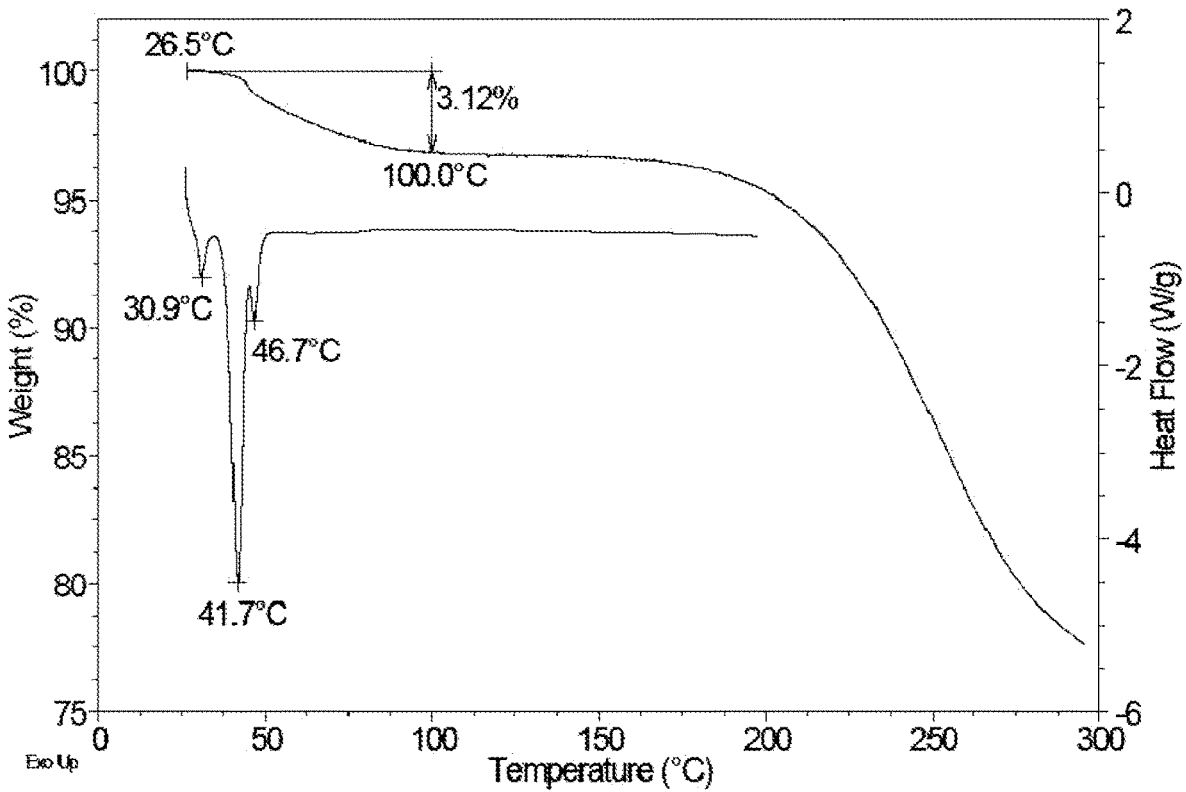
FIG. 7 shows the TGA/DSC curves of rotigotine behenate crystal form (Form II) in Example 4.

The XRPD data for the rotigotine behenate crystal form (Form II) are shown in Table 2, the powder X-ray diffraction results are shown in FIG. 5, and the TGA/DSC curves are shown in FIG. 7.

TABLE 2

Rotigotine behenate crystal form (Form II) XRPD data

| Pos. [°2Th.] | Height [cts] | FWHMLeft [°2Th.] | d-spacing [Å] | Rel. Int. [%] |
|---|---|---|---|---|
| 3.274108 | 129.297700 | 0.614016 | 26.98594 | 19.65 |
| 21.480630 | 657.882900 | 0.102336 | 4.13686 | 100.00 |
| 23.886770 | 260.269800 | 0.179088 | 3.72532 | 39.56 |

Comparative Example 1: Rotigotine Caprylate

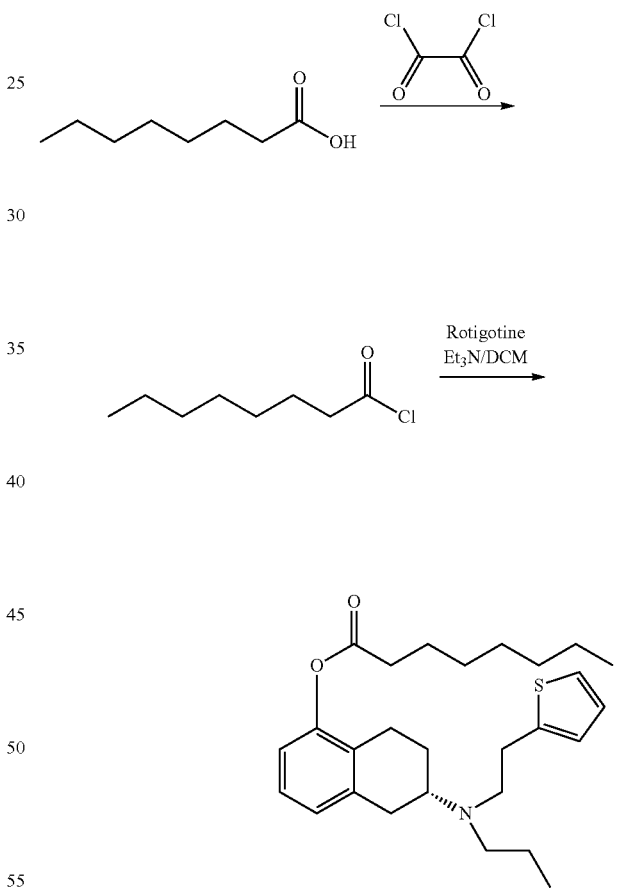

14.4 g (0.1 mol) of octanoic acid was dissolved in 300 ml of dichloromethane (DCM) under nitrogen at room temperature, and 12.7 g (0.1 mol) of oxalyl chloride was added dropwise to the above mixed solution within 30 min, and the resulting solution after completion of the reaction at room temperature was referred to as Solution I; 31.5 g (0.1 mol) of rotigotine was dissolved in a mixed solution containing 15.2 g (0.15 mol) of triethylamine and 300 ml of dichloromethane (DCM), which was referred to as solution II;

Solution I was added dropwise to Solution II. The above reaction solution was washed with an equal volume of water after completion of the reaction, and the solvent of the organic phase was evaporated under reduced pressure. The residue was purified by column chromatography eluting with a 1:3 (v/v) ethyl acetate-petroleum ether system as the eluent, to provide a light yellow oil (31.8 g) in a yield of 72.1%.

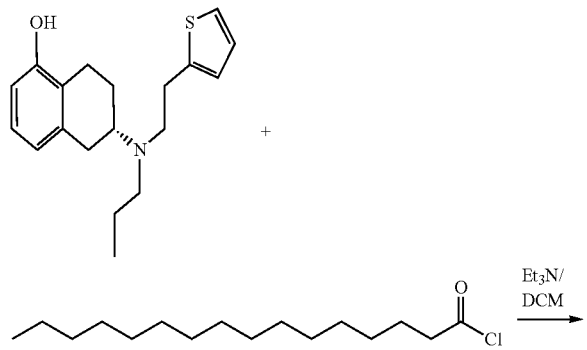

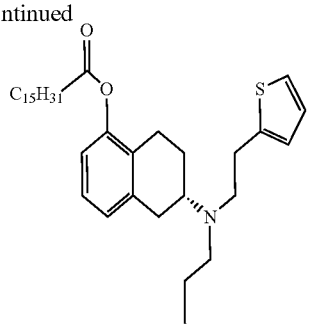

$^1$H NMR (CDCl$_3$, 400 MHz) δ$_H$: 7.01 (m, 2H, H-7 & H-14), 6.88 (d, J=7.56 Hz, 1H, H-6), 6.81 (t, J=3.46 Hz, 1H, H-15), 6.72 (t, J=2.78 Hz, 2H, H-8 & H-13), 2.92 (m 4H, H-1 & H-4), 2.78 (m, 4H, H-19 & H-20), 2.49 (m, 5H, H-2, H-22 & H-16), 2.04 (m, 1H, H-3), 1.77 (m, 2H, H-23), 1.58 (m, 1H, H-3), 1.39 (m, 2H, H-17), 1.23 (m, 8H, H-24-H-27), 0.96 (m, 6H, H-18 & H-28).

Comparative Example 2: Rotigotine Oleate

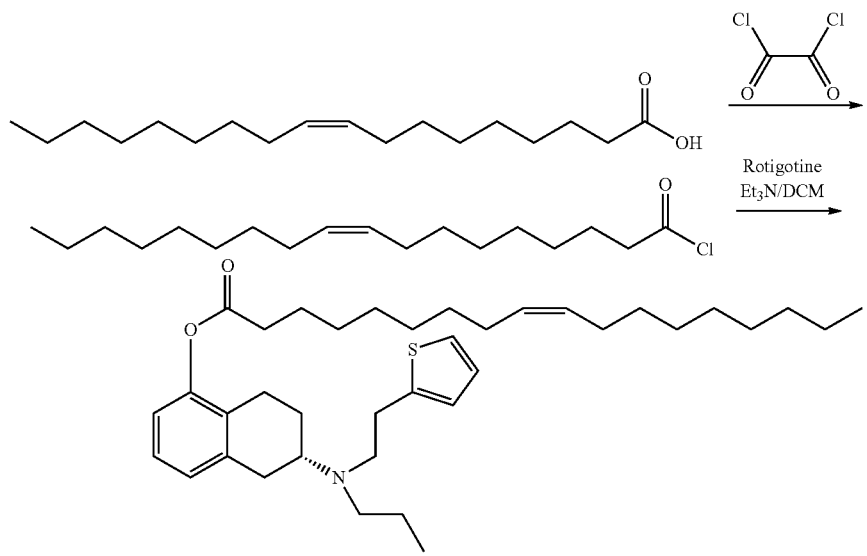

28.3 g (0.1 mol) of oleic acid was dissolved in 300 ml of dichloromethane (DCM) under nitrogen at room temperature, and 12.7 g (0.1 mol) of oxalyl chloride was added dropwise to the above mixed solution within 30 min, and the resulting solution after completion of the reaction at room temperature was referred to as Solution I; 31.5 g (0.1 mol) of rotigotine was dissolved in a mixed solution containing 15.2 g (0.15 mol) of triethylamine and 300 ml of dichloromethane (DCM), which was referred to as solution II; Solution I was added dropwise to Solution II to provide a reaction mixture. Upon completion of the reaction, the reaction mixture was washed with an equal volume of water, and the solvent of the organic phase was evaporated under reduced pressure. The residue was purified by column chromatography eluting with a 1:3 (v/v) ethyl acetate-petroleum ether system as the eluent, to provide a light yellow oil (40.1 g) in a yield of 69.1%.

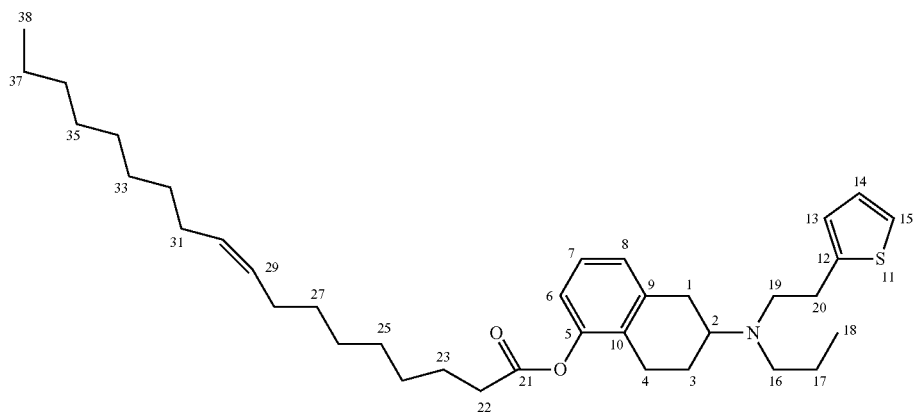 [SMILES: CCCCCCCC/C=C\CCCCCCCC(=O)Oc1cccc2c1CCC(N(CCC)CCc1cccs1)C2]

$^1$H NMR (CDCl$_3$, 400 MHz) δ$_H$: 7.10 (m, 2H, H-7 & H-14), 6.98 (d, J=7.58 Hz, 1H, H-6), 6.91 (t, J=3.48 Hz, 1H, H-15), 6.81 (t, J=2.80 Hz, 2H, H-8 & H-13), 5.42 (m 4H, H-29 & H-30), 2.94 (m 4H, H-1 & H-4), 2.80 (m, 4H, H-19 & H-20), 2.53 (m, 5H, H-2, H-22 & H-16), 2.04 (m, 5H, H-3, H-28 & H-31), 1.77 (m, 2H, H-23), 1.58 (m, 1H, H-3), 1.51 (m, 2H, H-37), 1.39 (m, 2H, H-17), 1.28 (m, 18H, H-24~H-27 & H-32~H-36), 0.89 (m, 6H, H-18 & H-38).

Comparative Example 3: Rotigotine Palmitate

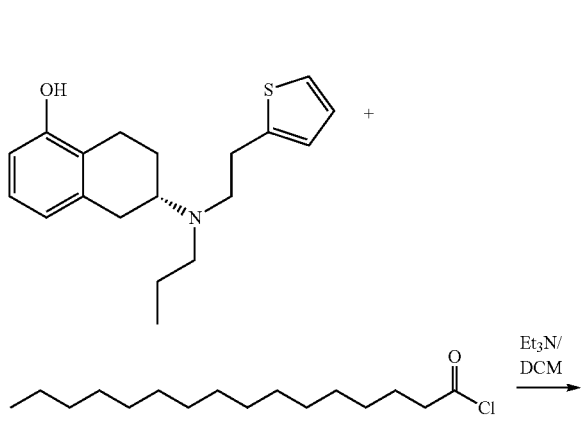

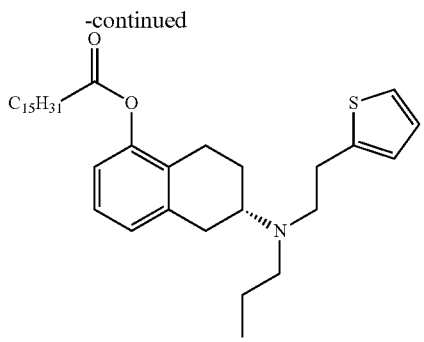

31.5 g (0.1 mol) of rotigotine was dissolved in a mixed solution containing 15.2 g (0.15 mol) of triethylamine and 300 ml of dichloromethane (DCM) under nitrogen at room temperature, and a mixed solution containing 27.49 g (0.1 mol) of palmitoyl chloride and 200 ml of dichloromethane (DCM) was added dropwise. The abovementioned reaction solution was washed with an equal volume of water after completion of the reaction, and the solvent of the organic phase was evaporated under reduced pressure. The residue was purified by column chromatography eluting with a 1:3 (v/v) ethyl acetate-petroleum ether system as the eluent, to provide a white-like solid (36.2 g) in a yield of 65.3%, melting point 27-30° C.

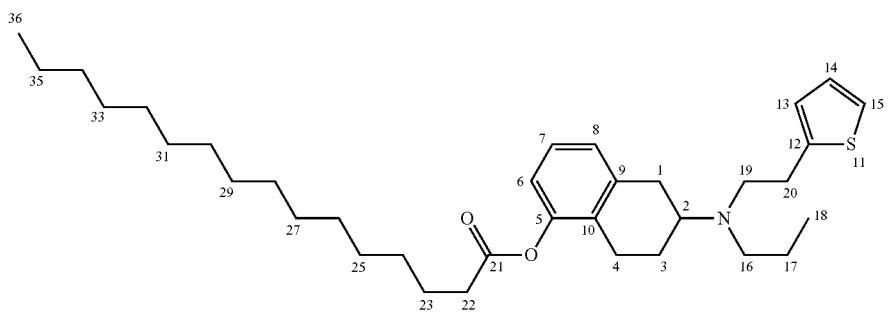

$^1$H NMR (CDCl$_3$, 400 MHz) δ$_H$: 7.11 (m, 2H, H-7 & H-14), 6.97 (d, J=7.64 Hz, 1H, H-6), 6.91 (t, J=3.52 Hz, 1H, H-15), 6.80 (t, J=2.84 Hz, 2H, H-8 & H-13), 2.92 (m 4H, H-1 & H-4), 2.79 (m, 4H, H-19 & H-20), 2.53 (m, 5H, H-2, H-22 & H-16), 2.03 (m, 1H, H-3), 1.76 (m, 2H, H-23), 1.55 (m, 1H, H-3), 1.49 (m, 2H, H-35), 1.38 (m, 2H, H-17), 1.26 (m, 22H, H-24~H-34), 0.88 (m, 6H, H-18 & H-36).

Comparative Example 4: Rotigotine Stearate

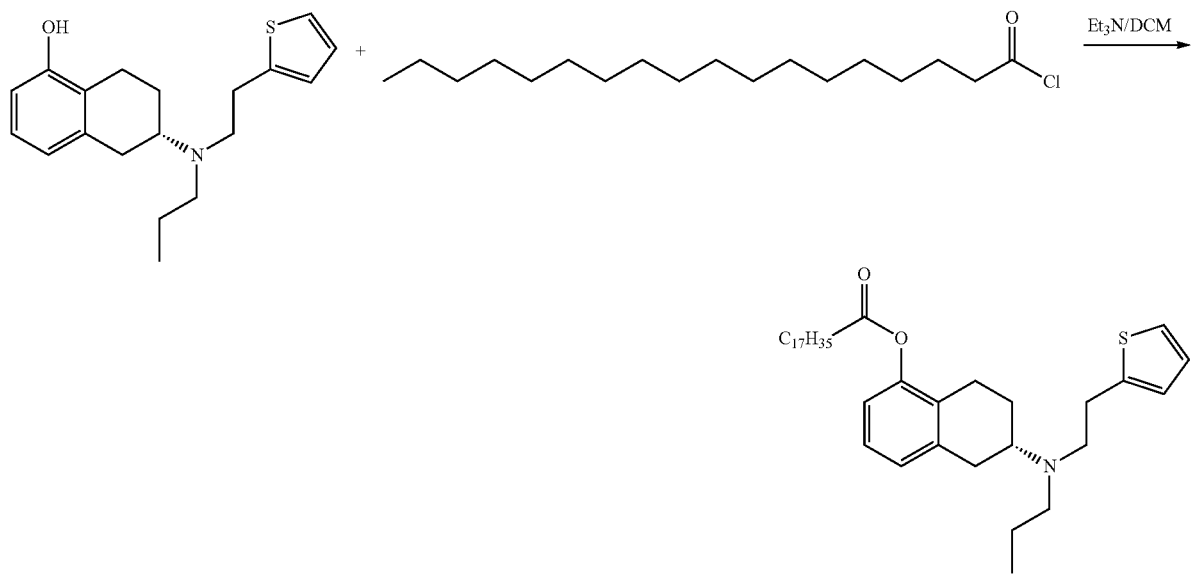

31.5 g (0.1 mol) of rotigotine was dissolved in a mixed solution containing 15.2 g (0.15 mol) of triethylamine and 300 ml of dichloromethane (DCM) under nitrogen at room temperature, and a mixed solution containing 30.29 g (0.1 mol) of stearyl chloride and 200 ml of dichloromethane (DCM) was added dropwise. The abovementioned reaction solution was washed with an equal volume of water after completion of the reaction, and the solvent of the organic phase was evaporated under reduced pressure. The residue was purified by column chromatography eluting with a 1:3 (v/v) ethyl acetate-petroleum ether system as the eluent, to provide a white-like solid (38.4 g) in a yield of 66.0%, melting point 24-26° C.

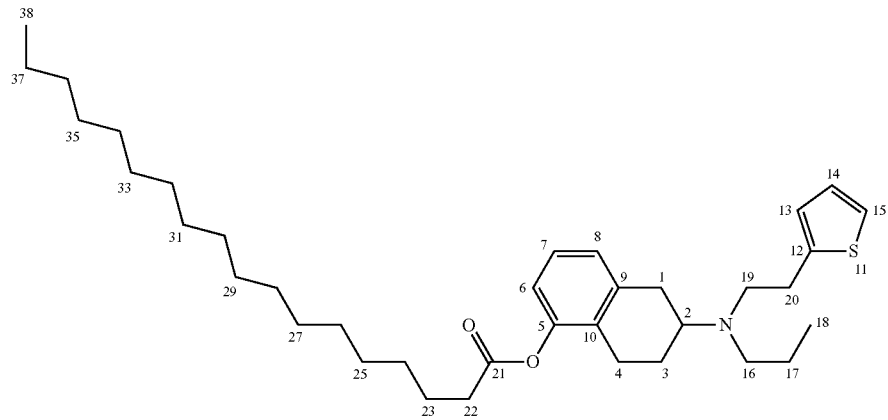

$^1$H NMR (CDCl$_3$, 400 MHz) $\delta_H$: 7.10 (m, 2H, H-7 & H-14), 6.98 (d, J=7.58 Hz, 1H, H-6), 6.91 (t, J=3.48 Hz, 1H, H-15), 6.81 (t, J=2.80 Hz, 2H, H-8 & H-13), 2.94 (m 4H, H-1 & H-4), 2.80 (m, 4H, H-19 & H-20), 2.53 (m, 5H, H-2, H-22 & H-16), 2.04 (m, 1H, H-3), 1.77 (m, 2H, H-23), 1.58 (m, 1H, H-3), 1.51 (m, 2H, H-37), 1.39 (m, 2H, H-17), 1.28 (m, 26H, H-24~H-36), 0.89 (m, 6H, H-18 & H-38).

Comparative Example 5: Rotigotine Arachidate

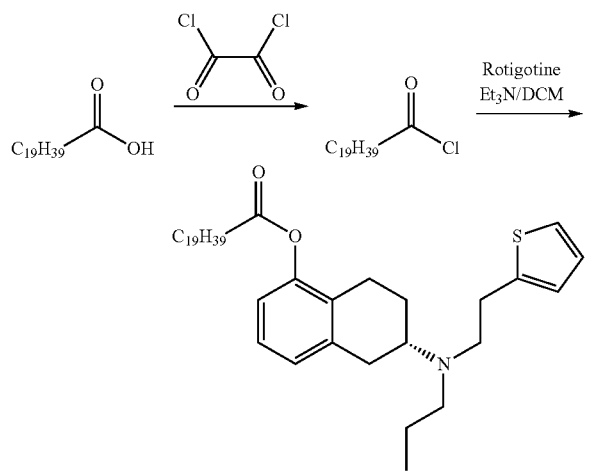

31.2 g (0.1 mol) of arachidic acid was dissolved in 300 ml of dichloromethane (DCM) under nitrogen at room temperature, and 12.7 g (0.1 mol) of oxalyl chloride was added dropwise to the mixed solution, the resulting solution after completion of the reaction was referred to as Solution I; 31.5 g (0.1 mol) of rotigotine was dissolved in a mixed solution containing 15.2 g (0.15 mol) of triethylamine and 300 ml of dichloromethane (DCM), which was referred to as Solution II; Solution I was added dropwise to Solution II; the abovementioned reaction solution was washed with an equal volume of water after completion of the reaction, and the solvent of the organic phase was evaporated under reduced pressure evaporated to give a oil, which was subjected to the subsequent cooling to provide a white solid. The white solid was washed with an appropriate amount of ethanol to give a white-like wet solid; after the abovementioned wet solid was dissolved in ethyl acetate by thermal dissolution, methanol was added to give a clear solution, followed by complete crystalization upon cooling; the mixture was filtered, and the filter cake was washed with an appropriate amount of methanol to provide a white-like solid (43.3 g) in a yield of 70.0%, melting point 30-33° C.

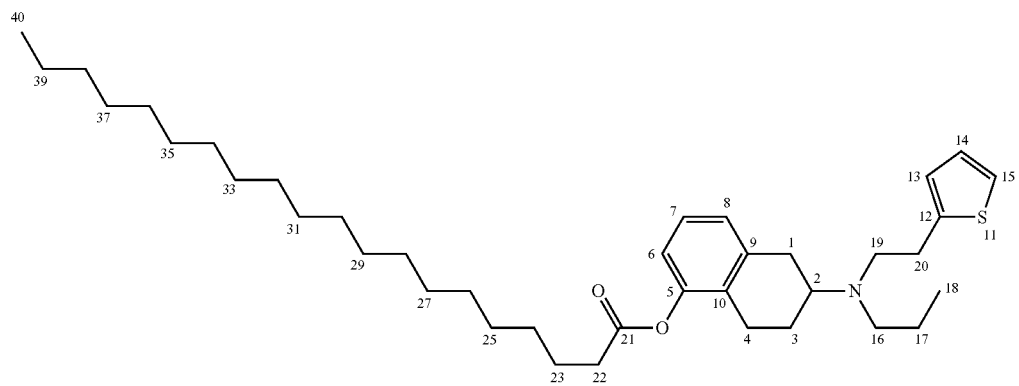 [SMILES: CCCCCCCCCCCCCCCCCCCC(=O)Oc1cccc2c1CCC(N(CCC)CCc1cccs1)C2]

$^1$H NMR (CDCl$_3$, 400 MHz) $\delta_H$: 7.10 (m, 2H, H-7 & H-14), 6.96 (d, J=7.56 Hz, 1H, H-6), 6.91 (q, J=3.40, 5.08 Hz, 1H, H-15), 6.80 (t, J=3.92 Hz, 2H, H-8 & H-13), □2.94 (m 4H, H-1 & H-4), 2.81 (m, 4H, H-19 & H-20), 2.53 (m, 5H, H-2, H-16 & H-22), 2.03 (m, 1H, H-3), 1.76 (m, 2H, H-23), 1.56 (m, 1H, H-3), 1.49 (m, 2H, H-39), 1.38 (m, 2H, H-17), 1.26 (m, 30H, H-24~H-38), 0.88 (m, 6H, H-18 & H-40).

Comparative Example 6: Rotigotine Lignocerate

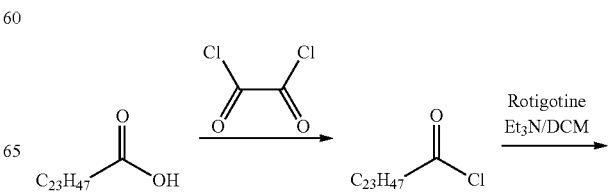

-continued

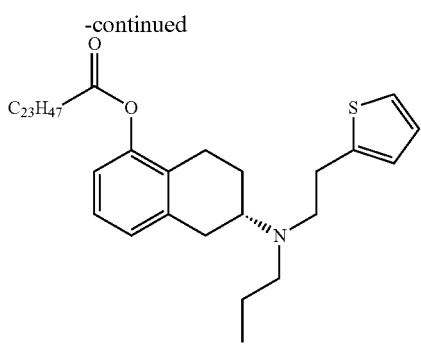

36.8 g (0.1 mol) of lignoceric acid was dissolved in 300 ml of dichloromethane (DCM) under nitrogen at room temperature, and 12.7 g (0.1 mol) of oxalyl chloride was added dropwise to the mixed solution, the resulting solution after completion of the reaction was referred to as Solution I; 31.5 g (0.1 mol) of rotigotine was dissolved in a mixed solution containing 15.2 g (0.15 mol) of triethylamine and 300 ml of dichloromethane (DCM), which was referred to as Solution II; Solution I was added dropwise to Solution II; the abovementioned reaction solution was washed with an equal volume of water after completion of the reaction, and the solvent of the organic phase was evaporated under reduced pressure evaporated to give a oil, which was subjected to the subsequent cooling to provide a white solid. The white solid was washed with an appropriate amount of ethanol to give a white-like wet solid; after the abovementioned wet solid was dissolved in ethyl acetate by thermal dissolution, methanol was added to give a clear solution, followed by complete crystallization upon cooling; the mixture was filtered, and the filter cake was washed with an appropriate amount of methanol to provide a white-like solid (46.6 g) in a yield of 70.0%, melting point 47-49° C.

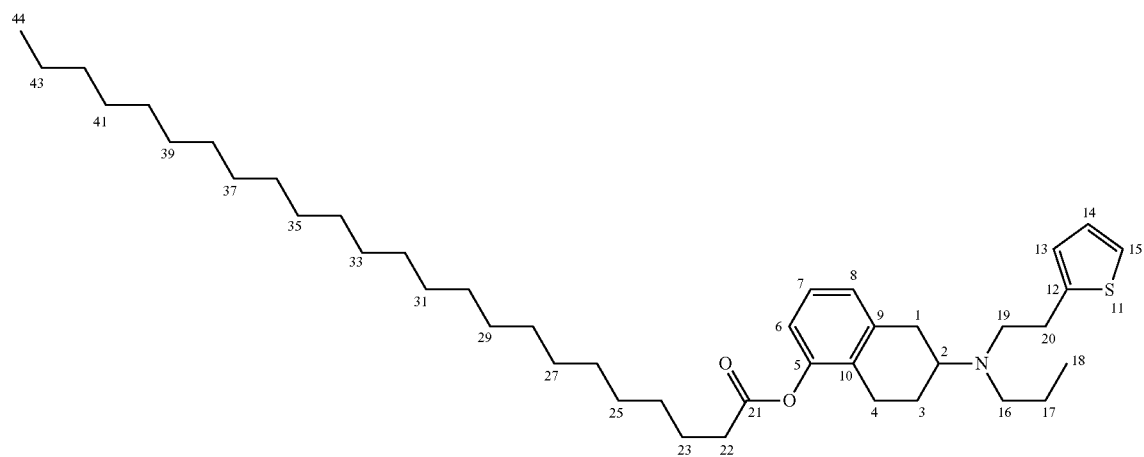 [SMILES: CCCCCCCCCCCCCCCCCCCCCCCC(=O)Oc1cccc2c1CCC(N(CCC)CCc1cccs1)C2]

$^1$H NMR (CDCl$_3$, 400 MHz) $\delta_H$: 7.11 (m, 2H, H-7 & H-14), 6.96 (d, J=7.36 Hz, 1H, H-6), 6.91 (q, J=3.42, 5.02 Hz, 1H, H-15), 6.81 (d, J=7.24 Hz, 2H, H-8 & H-13), 2.98 (m 4H, H-1 & H-4), 2.81 (m, 4H, H-19 & H-20), 2.53 (m, 5H, H-2, H-16 & H-22), 2.03 (m, 1H, H-3), 1.77 (m, 2H, H-23), 1.58 (m, 1H, H-3), 1.38 (m, 2H, H-43), 1.28 (m, 40H, H-17, H-24~H-42), 0.89 (m, 6H, H-18 & H-44).

Test Example 1: Pharmacokinetic Performance of Rotigotine Caprylate Injection in Rats Sample:
Rotigotine caprylate: prepared according to Comparative Example 1
HPMC: Shanghai Ka Le Kang Coating Technology Co., Ltd., Lot No: PD341942
Experimental Animals:
Male SD rats (provided by Shandong Luye Pharma Group Ltd.), weighing 190-280 g, 3 rats.
Test Process and Results:
Vehicle containing 1% of HPMC was prepared, and rotigotine caprylate was added to the vehicle to provide a 10 mg/ml of suspension (calculated as rotigotine). Three rats were intramuscularly injected with 2 mL/kg of the drug. Blood samples were taken from the eyelids of the rats before the administration (0 h) and at 0.25 h, 1 h, 6 h, 1 d, 2 d, 3 d, 5 d, 7 d, 9 d, 11 d, 14 d, 16 d, 18 d, 21 d, 24 d, 28 d after administration. Each blood sample was placed into heparinized EP tube, and was immediately centrifuged (3000 rpm) for 10 min. The plasma was separated and stored at −35° C. for testing.

Figure 8:
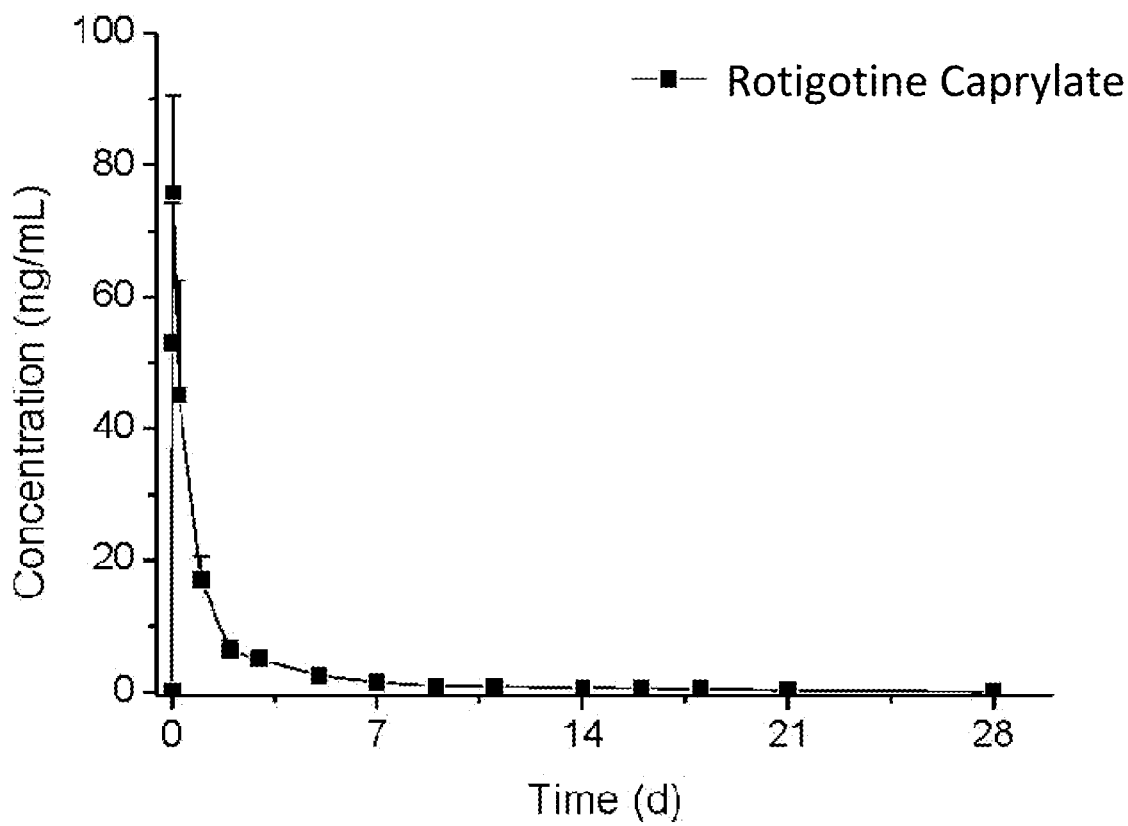
FIG. 8 shows the blood concentration-time curve of rotigotine after injection in rats in Test Example 1.

The mean blood concentrations (ng/mL) of rotigotine in rats at different time points are shown in Table 3. The blood concentration-time curve of rotigotine after injection in rats is shown in FIG. 8.

TABLE 3

| Blood concentration of rotigotine at different time points | | |
|---|---|---|
| Time (h) | Time (d) | Rotigotine caprylate |
| 0 | 0 | 0 |
| 0.25 | 0.01042 | 53.0 |
| 1 | 0.04167 | 75.8 |
| 6 | 0.25 | 45.1 |
| 24 | 1 | 16.97 |
| 48 | 2 | 6.27 |

TABLE 3-continued

Blood concentration of rotigotine at different time points

| Time (h) | Time (d) | Rotigotine caprylate |
|---|---|---|
| 72 | 3 | 4.94 |
| 120 | 5 | 2.46 |
| 168 | 7 | 1.48 |
| 216 | 9 | 0.91 |
| 264 | 11 | 0.82 |
| 336 | 14 | 0.65 |
| 384 | 16 | 0.53 |
| 432 | 18 | 0.51 |
| 504 | 21 | 0.29 |
| 576 | 24 | 0.10 |
| 672 | 28 | 0 |

Conclusion

It can be seen from Table 3 and FIG. 8 that the intramuscular injection of rotigotine caprylate in rats reaches the blood concentration peak in 1 hour, the blood concentration fluctuates significantly, and the effective blood concentration is maintained only for a short period of time, and long-term steady release cannot be achieved.

Test Example 2: Pharmacokinetic Performance of Each Drug Injection in Rats

Samples:

Rotigotine oleate: prepared according to Comparative Example 2;

Rotigotine palmitate: prepared according to Comparative Example 3;

Rotigotine stearate: prepared according to Comparative Example 4;

Rotigotine hydrochloride: purity of 99.83%

HPMC: Shanghai Ka Le Kang Coating Technology Co., Ltd. Lot No.: PD341942

Experimental animals: Male SD rats (provided by Shandong Luye Pharma Group Ltd.), weighing 190-280 g, 12 rats in total, 3 rats in each group.

Test Process and Results:

Vehicle containing 1% of HPMC was prepared, and rotigotine oleate, rotigotine palmitate and rotigotine stearate were added to the vehicle respectively to provide 10 mg/ml of suspensions (calculated as rotigotine). Rotigotine hydrochloride was formulated as a 0.36 mg/ml injection (calculated as rotigotine) in normal saline.

The experimental animals were randomly divided into rotigotine oleate group (A), rotigotine palmitate group (B), rotigotine stearate group (C) and rotigotine hydrochloride group (D), with 3 rats in each group. The rats in Groups A, B, and C were intramuscularly injected with the corresponding drug (2 ml/kg), and the rats in group D were injected intravenously with the corresponding drug (2 ml/kg).

Blood samples were taken from the eyelids of the rats in Groups A, B, and C before the administration (0 h) and at 0.25 h, 1 h, 6 h, 1 d, 2 d, 3 d, 5 d, 7 d, 9 d, 11 d, 14 d, 16 d, 18 d, 21 d, 24 d, 28 d after administration. Each sample was placed into heparinized EP tube, and was immediately centrifuged (3000 rpm) for 10 min. The plasma was separated and stored at −35° C. for testing.

Blood samples were taken from the eyelids of the rats in Group D before the administration (0 h) and at 3 min, 10 min, 0.25 h, 0.5 h, 1 h, 1.5 h, 2 h, 4 h, 6 h, 8 h, and 12 h after administration. Each blood sample was placed into heparinized EP tube, and was immediately centrifuged (3000 rpm) for 10 min. The plasma was separated and stored at −35° C. for testing.

Figure 9:
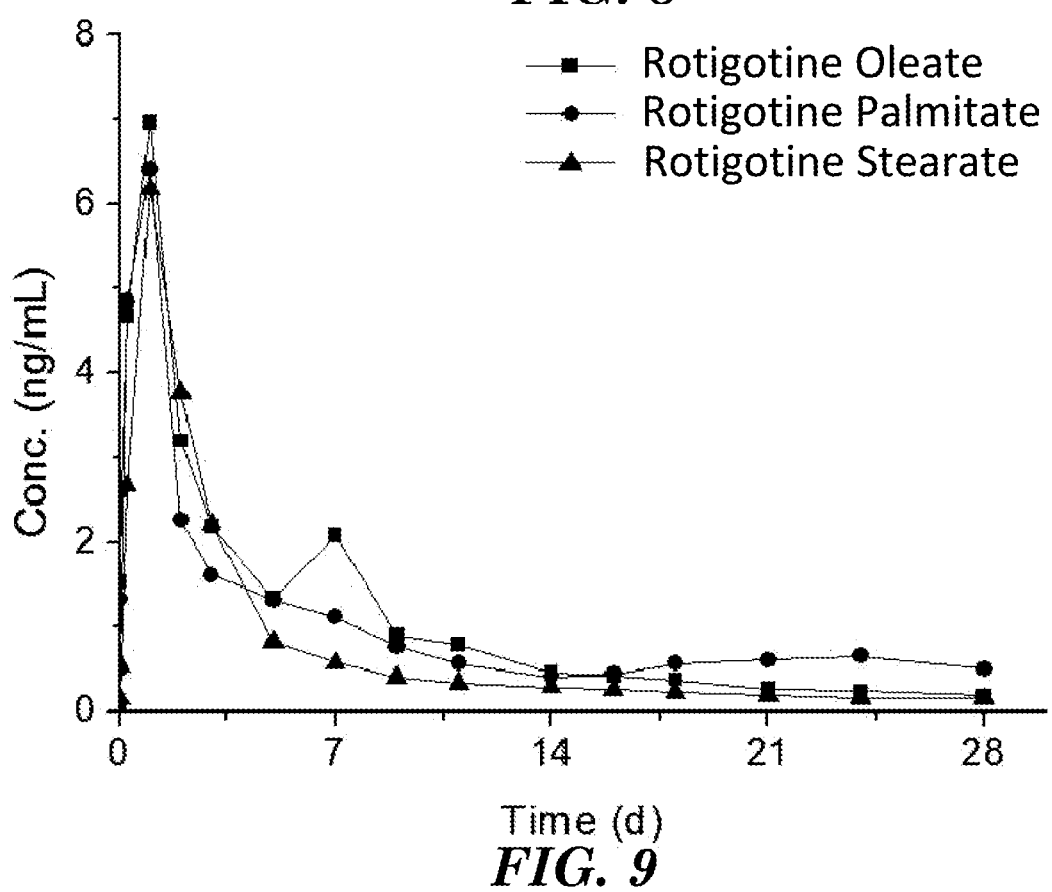
FIG. 9 shows the blood concentration-time curve of rotigotine after injection in rats in Test Example 2.

The blood concentrations (ng/mL) of rotigotine in rats at different time points are shown in Tables 4 and 5. The blood concentration-time curve of rotigotine after injection in rats is shown in FIG. 9.

TABLE 4

Blood concentration of rotigotine at different time points

| Time (h) | Time (d) | Rotigotine oleate | Rotigotine palmitate | Rotigotine stearate |
|---|---|---|---|---|
| 0 | 0 | 0 | 0 | 0 |
| 0.25 | 0.01042 | 1.53 | 0.51 | 0.15 |
| 1 | 0.04167 | 2.61 | 1.33 | 0.54 |
| 6 | 0.25 | 4.67 | 4.85 | 2.67 |
| 24 | 1 | 6.97 | 6.41 | 6.18 |
| 48 | 2 | 3.20 | 2.26 | 3.78 |
| 72 | 3 | 2.19 | 1.62 | 2.21 |
| 120 | 5 | 1.34 | 1.32 | 0.83 |
| 168 | 7 | 2.08 | 1.12 | 0.58 |
| 216 | 9 | 0.90 | 0.77 | 0.41 |
| 264 | 11 | 0.80 | 0.57 | 0.34 |
| 336 | 14 | 0.46 | 0.41 | 0.29 |
| 384 | 16 | 0.42 | 0.45 | 0.27 |
| 432 | 18 | 0.38 | 0.57 | 0.23 |
| 504 | 21 | 0.27 | 0.61 | 0.20 |
| 576 | 24 | 0.24 | 0.66 | 0.16 |
| 672 | 28 | 0.19 | 0.51 | 0.15 |

TABLE 5

Blood concentration in rats at different time points

| Time (h) | Rotigotine |
|---|---|
| 0 | 0 |
| 0.05 | 82.48 |
| 0.17 | 43.78 |
| 0.25 | 45.39 |
| 0.5 | 28.97 |
| 1 | 12.12 |
| 1.5 | 7.25 |
| 2 | 4.71 |
| 4 | 0.99 |
| 8 | 0.16 |
| 12 | 0.04 |

Conclusion

As seen from Table 4, Table 5 and FIG. 9, after intramuscular injection of the corresponding drugs in rats, the drugs in different groups reached the blood concentration peak in body early. The blood concentrations fluctuated significantly and the effective blood concentration was maintained only for a short period of time, which would not achieve the long-term steady release for more than two weeks. Additionally, the absolute bioavailability of above drugs is low, with the absolute bioavailability of rotigotine oleate, rotigotine palmitate and rotigotine stearate being 54.3%, 51.3% and 38.2%, respectively.

Test Example 3: Pharmacokinetic Performance of Each Drug Injection in Rats

Samples:

Rotigotine arachidate: prepared according to Comparative Example 5;

Rotigotine behenate: prepared according to Example 1;

Rotigotine lignocerate: prepared according to Comparative Example 6;

HPMC: Shanghai Ka Le Kang Coating Technology Co., Ltd. Lot No.: PD341942

Experimental Animals:

Male SD rats (provided by Shandong Luye Pharma Group Ltd.), weighing 190-280 g, 12 rats, 3 rats in each group.

Test Process and Results:

Vehicle containing 1% of HPMC was prepared, and rotigotine arachidate, rotigotine behenate and rotigotine lignocerate were added to the vehicle respectively to provide 10 mg/ml of suspensions (calculated as rotigotine).

The experimental animals were randomly divided into rotigotine arachidate group (A), rotigotine behenate group (B) and rotigotine lignocerate group (C), with 3 rats in each group, The rats in Groups A, B and C were intramuscularly injected with the corresponding drug (2 ml/kg).

Blood samples were taken from the eyelids of the rats in Groups A, B, and C before the administration (0 h) and at 0.25 h, 1 h, 6 h, 1 d, 2 d, 3 d, 5 d, 7 d, 9 d, 11 d, 14 d, 16 d, 18 d, 21 d, 25 d, 28 d, 30 d, 35 d, 39 d, 42 d after administration. Each blood sample was placed into heparinized EP tube, and was immediately centrifuged (3000 rpm) for 10 min. The plasma was separated and stored at −35° C. for testing.

Figure 10:
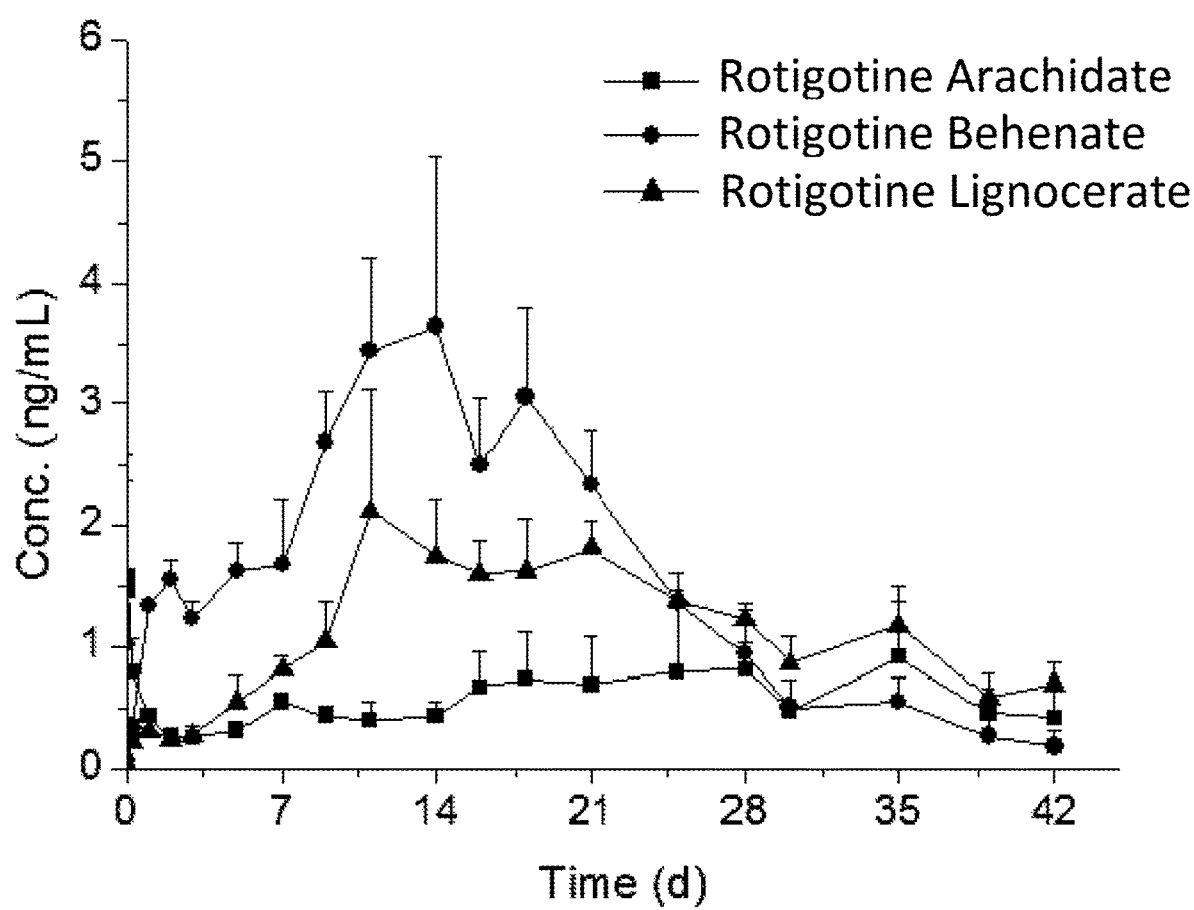
FIG. 10 shows the blood concentration-time curve of rotigotine after injection in rats in Test Example 3.

The blood concentrations (ng/mL) of rotigotine in rats at different time points are displayed in Table 6. The blood concentration-time curve of rotigotine after injection in rats is shown in FIG. 10.

TABLE 6

Blood concentration of rotigotine at different time points

| Time (d) | Time (h) | Rotigotine arachidate | Rotigotine behenate | Rotigotine lignocerate |
|---|---|---|---|---|
| 0 | 0 | 0 | 0 | 0 |
| 0.010417 | 0.25 | 1.45 | 1.01 | 0.231 |
| 0.041667 | 1 | 1.56 | 0.070 | 0.310 |
| 0.25 | 6 | 0.788 | 0.332 | 0.231 |
| 1 | 24 | 0.427 | 1.34 | 0.316 |
| 2 | 48 | 0.246 | 1.56 | 0.236 |
| 3 | 72 | 0.258 | 1.23 | 0.274 |
| 5 | 120 | 0.315 | 1.63 | 0.551 |
| 7 | 168 | 0.546 | 1.68 | 0.816 |
| 9 | 216 | 0.429 | 2.68 | 1.04 |
| 11 | 264 | 0.403 | 3.44 | 2.12 |
| 14 | 336 | 0.427 | 3.64 | 1.75 |
| 16 | 384 | 0.665 | 2.50 | 1.60 |
| 18 | 432 | 0.733 | 3.05 | 1.63 |
| 21 | 504 | 0.684 | 2.34 | 1.81 |
| 25 | 600 | 0.793 | 1.36 | 1.38 |
| 28 | 672 | 0.814 | 0.940 | 1.23 |
| 30 | 720 | 0.473 | 0.503 | 0.870 |
| 35 | 840 | 0.911 | 0.547 | 1.17 |
| 39 | 936 | 0.462 | 0.269 | 0.581 |
| 42 | 1032 | 0.415 | 0.183 | 0.693 |

Conclusion:

As seen from Table 6, Table 5 and FIG. 10, after intramuscular injection of the corresponding drugs, the release of rotigotine arachidate was high in the early stage in vivo, the blood concentration was low during the release period, and the effective blood concentration was maintained only for a short period of time, the absolute bioavailability of intramuscular injection of rotigotine arachidate was 33.1%. For rotigotine lignocerate, the release in the early stage was low, and the effective blood concentration could not be obtained in the early stage. The absolute bioavailability of rotigotine lignocerate was 65.2%. In contrast, the release of rotigotine behenate in vivo has no delay period, the effective blood concentration was steady and the maintenance period can reach more than two weeks. The absolute bioavailability of intramuscular injection to the rat is 91.1%. The results of Test Examples 1-3 indicate that the unsaturated carboxylic acid ester of rotigotine, such as rotigotine oleate, reaches the blood concentration peak in body early, and the blood concentration fluctuates significantly and the effective blood concentration is maintained only for a short period of time. Rotigotine octanoate, a specific saturated carboxylic acid ester of rotigotine, reaches the blood concentration peak in body in 1 hour, and the effective blood concentration is maintained only for a short period of time. Other saturated long-chain esters, such as rotigotine palmitate and rotigotine stearate, have blood concentrations which fluctuate significantly, and the effective blood concentrations are maintained only for a short period of time which is no more than two weeks. Although the blood concentrations of rotigotine arachidate and rotigotine lignocerate do not fluctuate significantly, their effective blood concentration cannot be maintained for more than two weeks. None of the aforementioned saturated or unsaturated long-chain carboxylic acid esters of rotigotine has an absolute bioavailability equal to or higher than 70%. Only rotigotine behenate has an absolute bioavailability of higher than 90%. Its effective blood concentration shows little fluctuation and can be maintained for more than two weeks. Rotigotine behenate is thus demonstrated to have achieved the effects of reducing the fluctuation of blood concentration, improving the bioavailability in vivo, and maintaining the smooth and steady release for more than two weeks.

The invention claimed is:

1. Rotigotine behenate as shown in Formula:

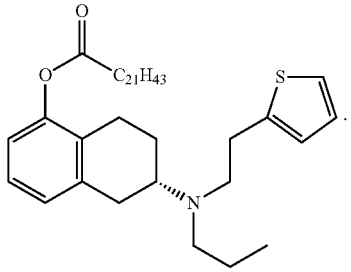

wherein the rotigotine behenate is in crystal Form I having characteristic peaks expressed in degrees 2θ(±0.2 2θ) at 21.563, 21.156, 23.295, 21.955 and 20.838 in a powder X-ray diffraction pattern obtained using CuKα radiation.

2. Rotigotine behenate in crystal Form I according to claim 1 having characteristic peaks expressed in degrees 2θ(±0.2 2θ) at 21.563, 21.156, 23.295, 21.955, 20.838, 16.154, 19.403, 11.749, 14.518 and 17.875.

3. Rotigotine behenate in crystal Form I according to claim 2 having characteristic peaks expressed in degrees 2θ(±0.2 2θ) at 21.563, 21.156, 23.295, 21.955, 20.838, 16.154, 19.403, 11.749, 14.518, 17.875, 19.729, 20.299, 13.589, 11.962, 22.949, 23.772, 16.424, 15.749, 12.586, and 22.430.

4. Rotigotine behenate in crystal Form I according to claim 3 having characteristic peaks expressed in degrees 2θ(±0.2 2θ) at 21.563, 21.156, 23.295, 21.955, 20.838, 16.154, 19.403, 11.749, 14.518, 17.875, 19.729, 20.299, 13.583, 11.962, 22.949, 23.772, 16.424, 15.749, 12.586, 22.430, 12.238, 23.995, 18.626, 16.614, 28.574, 24.530, 25.169, 27.044, 36.329, 27.764, 29.127, and 31.490.

5. Rotigotine behenate in crystal Form I according to claim 4 characterized by a powder X-ray diffraction pattern substantially as shown in FIG. 4.

6. A method for preparing rotigotine behenate in crystal Form I according to claim 1, the method comprising thermally dissolving rotigotine behenate in ethyl acetate, adding methanol, cooling and crystallizing to provide a suspension of crystals, filtering the suspension, washing the crystals with methanol to provide the crystal Form I of rotigotine behenate.

7. Rotigotine behenate as shown in Formula

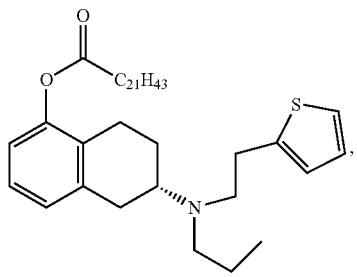

wherein the rotigotine behenate is in crystal Form II having characteristic peaks expressed in degrees 2θ(±0.2 2θ) at 21.481, 23.887 in a powder X-ray diffraction pattern obtained using CuKα radiation.

8. Rotigotine behenate in crystal Form II according to claim 7, having characteristic peaks expressed in degrees 2θ(±0.2 2θ) at 3.274, 21.481, 23.887.

9. Rotigotine behenate in crystal Form II according to claim 8, characterized by a powder X-ray diffraction pattern substantially as shown in FIG. 5.

10. A method for preparing rotigotine behenate in crystal Form II according to claim 7, the method comprising: suspending rotigotine behenate in a mixed solvent of tetrahydrofuran and methanol at 1:19 (v/v) to provide a suspension, and stirring the suspension at 40° C. for 5 days to provide the crystal Form II of rotigotine behenate.

11. A pharmaceutical composition comprising the rotigotine behenate according to claim 1 and a pharmaceutically acceptable excipient.

12. The composition according to claim 11, wherein the composition is in a parenteral form.

13. Rotigotine behenate in crystal Form I according to claim 1, having a TGA/DSC curves substantially as shown in FIG. 6.

14. Rotigotine behenate in crystal Form II according to claim 7, having a TGA/DSC curves substantially as shown in FIG. 7.

15. A pharmaceutical composition comprising the rotigotine behenate according to claim 7 and a pharmaceutically acceptable excipient.

16. The composition according to claim 15, wherein the composition is in a parenteral form.

* * * * *